United States Patent [19]

Weterings et al.

[11] Patent Number: 5,415,695
[45] Date of Patent: * May 16, 1995

[54] METHOD OF PREPARING SOLID LACTULOSE

[75] Inventors: Hendrikus W. Weterings; Hendrik Pluim, both of Weesp, Netherlands

[73] Assignee: Duphar International Research B.V., Weesp, Netherlands

[*] Notice: The portion of the term of this patent subsequent to Jul. 5, 2011 has been disclaimed.

[21] Appl. No.: 175,184

[22] Filed: Dec. 29, 1993

Related U.S. Application Data

[63] Continuation of Ser. No. 686,854, Apr. 18, 1991, abandoned, which is a continuation of Ser. No. 322,889, Mar. 15, 1989, abandoned.

[30] Foreign Application Priority Data

Mar. 18, 1988 [NL] Netherlands .......................... 8800678

[51] Int. Cl.$^6$ .......................... C13F 1/02; C13F 3/00; C07H 1/00; C08B 37/00
[52] U.S. Cl. ........................ 127/58; 127/29; 127/30; 127/63; 536/124; 536/125
[58] Field of Search ........................ 127/29, 30, 58, 63; 536/124, 125

[56] References Cited

U.S. PATENT DOCUMENTS

| | | | |
|---|---|---|---|
| 3,110,600 | 11/1963 | Bok | 426/71 |
| 3,562,012 | 2/1971 | Reinicke et al. | 127/29 |
| 3,692,766 | 9/1972 | Reinicke et al. | 536/121 |
| 3,716,408 | 2/1973 | Nagasawa et al. | 127/29 |
| 3,816,394 | 6/1974 | Nagasawa et al. | 536/124 |
| 4,142,916 | 3/1979 | Ogasa et al. | 127/30 |
| 4,931,554 | 6/1990 | Bijl et al. | 536/124 |
| 5,003,061 | 3/1991 | Carobbi et al. | 127/30 |

FOREIGN PATENT DOCUMENTS

| | | |
|---|---|---|
| 0318630 | 6/1989 | European Pat. Off. . |
| 0333295 | 9/1989 | European Pat. Off. . |
| 2717707 | 3/1979 | Germany . |
| 61-104800 | 4/1986 | Japan .......................... C13K 13/00 |
| 129368 | 12/1970 | Netherlands . |

OTHER PUBLICATIONS

*Chemical Abstracts*, vol. 81, No. 24, Dec. 16, 1974, p. 150, Abstract No. 154959d, Nagasawa, et al; "High Purity Lactulose Powder," Japan Kokai 74 54, 556, May 1974.

Journal of Pharmaceutical Sciences, vol. 73 No. 10, Oct. 1984, Reijke et al, "Relationship between Refractive Index and Dry Substance Content for Lactulose Syrups," pp. 1478–1479.

*Primary Examiner*—Paul Lieberman
*Assistant Examiner*—Patricia L. Hailey
*Attorney, Agent, or Firm*—Stevens, Davis, Miller & Mosher

[57] ABSTRACT

The invention relates to a method of preparing solid forms of administration of lactulose by evaporating lactulose syrup to a water content of at most 10%, preferably 2 to 6%, cooling the thick, evaporated syrup, grinding and sieving, or breaking the solid product.

3 Claims, No Drawings

METHOD OF PREPARING SOLID LACTULOSE

This application is a continuation of application Ser. No. 07/686,954, filed Apr. 18, 1991, now abandoned, which is a continuation of application Ser. No. 07/322,889, filed Mar. 15, 1989, and now abandoned.

The invention relates to a method of preparing solid forms of administration of lactulose from lactulose syrup.

Netherlands Patent Specifications No. 129368, 147784 and 150161 relate to methods of preparing solid forms of administration of lactulose. They relate to lactulose in powder form obtained by spray-drying lactulose syrup. The drawback of this method is that spray-drying of lactulose requires a vehicle. As a result of this the content of lactulose in the final product will always be lower than in the syrup. Moreover, the use of a vehicle has a price-raising effect.

Furthermore, German Patent Specification No. 2717707 relates to a method of preparing a solid form of administration of lactulose by heating a water-containing solution of lactulose which also comprises auxiliary substances for the caramelisation, while evaporating water so that upon cooling solid lactulose is obtained in a caramelised form. A drawback of this product is that, as a result of the caramelisation, it experiences a strong colouring, which is undesired for a pharmaceutical product.

Finally it is possible to prepare lactulose in a crystalline form. However, the crystallisation of lactulose is rather laborious and the crystalline final product comprises a certain quantity of the solvent used (customarily methanol). Crystallisation increases the cost of production considerably.

It is the object of the present invention to provide a solid form of administration of lactulose which is simple to prepare and which does not exhibit the drawbacks of the known products mentioned hereinbefore.

It has now been found that a solid form of administration of lactulose can be obtained which qualitatively is comparable to the syrup used as the starting material, by evaporating the syrup to a water content of at most 10%, then cooling, grinding and sieving, or breaking the solid lactulose syrup.

The evaporation of the lactulose syrup is carried out by rapidly heating it for a short period of time. This is preferably done under reduced pressure so that evaporation can be carried out at lower temperatures, for example, in a rotating film evaporator. The pressure at which evaporation is carried out depends on the apparatus used. The syrup is preferably evaporated to a water content of from 2 to 6%.

The evaporated hot, thick syrup the final temperature of which when leaving the evaporator is chosen above the solidification point of lactulose (about 100° C.) is then cooled to approximately 20° C. During this step the syrup solidifies.

By cooling in such a manner, that is, as rapidly as possible or in a conditioned space (low humidity) so that hardly any or no water can be attracted from the air, it is achieved that the evaporated solid syrup does not stick so that further mechanical processing is possible. It has been found that the quality of the final product both after rapid cooling in air, and after slow cooling in a conditioned space is comparable.

It has further been found that the formulation properties of the final product, for example, dissolving rate and hygroscopicity, depend on the particle size chosen.

The starting syrup is preferably evaporated to a water content of from 2 to 6% at an as low as possible temperature and pressure so as to prevent decomposition.

The invention will now be described in greater detail with reference to the ensuing specific example.

EXAMPLE

Evaporation was carried out in a rotating film evaporator of the brand Canzler having a heated surface area of 1 m². The parameters to be adjusted are:
1) $\phi_v$, i.e. the quantity supplied to the evaporator (feed stream)
2) $P_v$, i.e. the pressure in the evaporator
3) $P_s$, i.e. the pressure of the steam to heat the evaporator, and/or the steam temperature.

These parameters should be chosen to be so that the final temperature ($T_e$) of the evaporated syrup emanating from the evaporator is higher than the solidification point of about 100° C.

| $\phi_v(m^3/h)$ | $P_v(10^5\ Pa)$ | $P_s(10^5\ Pa)$ | $T_e(°C.)$ | % $H_2O$ |
|---|---|---|---|---|
| 0.0980 | 0.57 | 1.73 | 124 | 5–5.7 |
| 0.054 | 0.60 | 2.80 | 138 | 2.9–4 |

The cooling of the evaporated syrup was carried out
a) on a cooling roller (drum flaker) so that flakes are obtained
b) with a rotadropformer + cooling belt so that pastils are obtained
c) by slowly cooling in a closed pot.

Solid lactulose which does substantially not stick and can readily be subjected to further processing, for example, grinding or breaking, sieving and packaging, is obtained both after accelerated cooling in air and after slow cooling in a closed pot.

We claim:

1. A method of preparing a solid form of administration of lactulose from lactulose syrup, consisting essentially of evaporating lactulose syrup to a water content of at most 10%, cooling the evaporated lactulose syrup, and grinding and sieving, or breaking, the solid lactulose.

2. The method as claimed in claim 1, wherein the evaporated syrup is cooled as rapidly as possible in air or in a conditioned, moisture-free space.

3. The method as claimed in claim 1, wherein the syrup is evaporated in a rotating film evaporator to a water content of from 2 to 6%.

* * * * *